United States Patent
Yu et al.

(10) Patent No.: US 11,119,087 B2
(45) Date of Patent: Sep. 14, 2021

(54) METHOD FOR VERIFYING REGENERATION EFFECT BETWEEN ANTIOXIDANTS THROUGH ESTABLISHING A SEPARABLE REGENERATION SYSTEM

(71) Applicant: Jiangnan University, Jiangsu (CN)

(72) Inventors: Hang Yu, Jiangsu (CN); Yaxin He, Jiangsu (CN); Yunfei Xie, Jiangsu (CN); Yahui Guo, Jiangsu (CN); Yuliang Cheng, Jiangsu (CN); Weirong Yao, Jiangsu (CN)

(73) Assignee: Jiangnan University, Wuxi (CN)

( * ) Notice: Subject to any disclaimer, the term of this patent is extended or adjusted under 35 U.S.C. 154(b) by 247 days.

(21) Appl. No.: 16/460,635

(22) Filed: Jul. 2, 2019

(65) Prior Publication Data
US 2020/0363388 A1 Nov. 19, 2020

(30) Foreign Application Priority Data
May 16, 2019 (CN) .......................... 201910409989.4

(51) Int. Cl.
| | |
|---|---|
| *G01N 33/02* | (2006.01) |
| *A23G 1/42* | (2006.01) |
| *A23G 1/54* | (2006.01) |

(52) U.S. Cl.
CPC ............. *G01N 33/02* (2013.01); *A23G 1/426* (2013.01); *A23G 1/545* (2013.01); *A23V 2002/00* (2013.01)

(58) Field of Classification Search
CPC .... A23G 1/426; A23G 1/545; A23V 2002/00; G01N 33/02; Y10T 436/142222; Y10T 436/203332; Y10T 436/25
USPC ...................................... 436/20, 93, 131, 174
See application file for complete search history.

(56) References Cited

U.S. PATENT DOCUMENTS

2005/0087452 A1* 4/2005 McAnalley .......... A61K 31/355
205/777.5

OTHER PUBLICATIONS

Guo et al. Food Research International, vol. 95, Feb. 20, 2017, pp. 1-8.*

* cited by examiner

*Primary Examiner* — Maureen Wallenhorst
(74) *Attorney, Agent, or Firm* — Muncy, Geissler, Olds & Lowe, P.C.

(57) ABSTRACT

The invention provides a method for establishing a separable regeneration system for verifying regeneration effect between two antioxidants, which belongs to the field of regeneration effect of antioxidants. According to different solubilities of two antioxidants, lipid-soluble antioxidant is first combined into PE film, and water-soluble antioxidant is dissolved into deionized water and a separable regeneration system where antioxidants can contact with other but not dissolve in each other is formed. This method compares the differences of change of antioxidant capacity in aqueous phase with and without lipid-soluble antioxidant so that to judge whether the added lipid-soluble antioxidant has regeneration effect on aqueous-soluble antioxidant. The present invention effectively verifies the regeneration effect between different antioxidants, and has advantages of simple operation, less interference factors, intuitive and high efficiency.

10 Claims, 1 Drawing Sheet

(FIG. 1 as an illustration in Abstract)

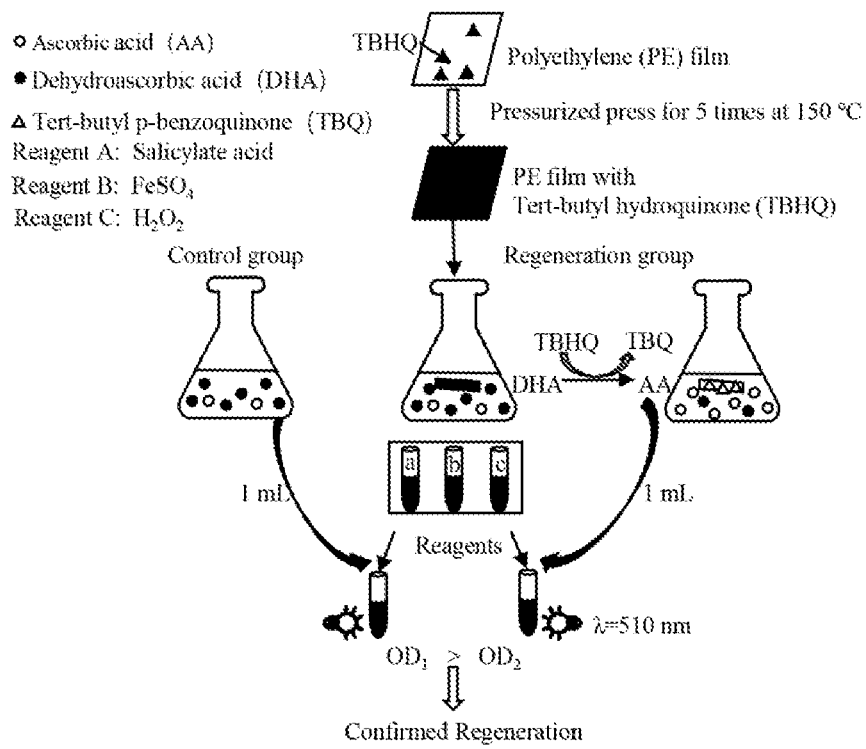
FIG. 1 (FIG. 1 as an illustration in Abstract)
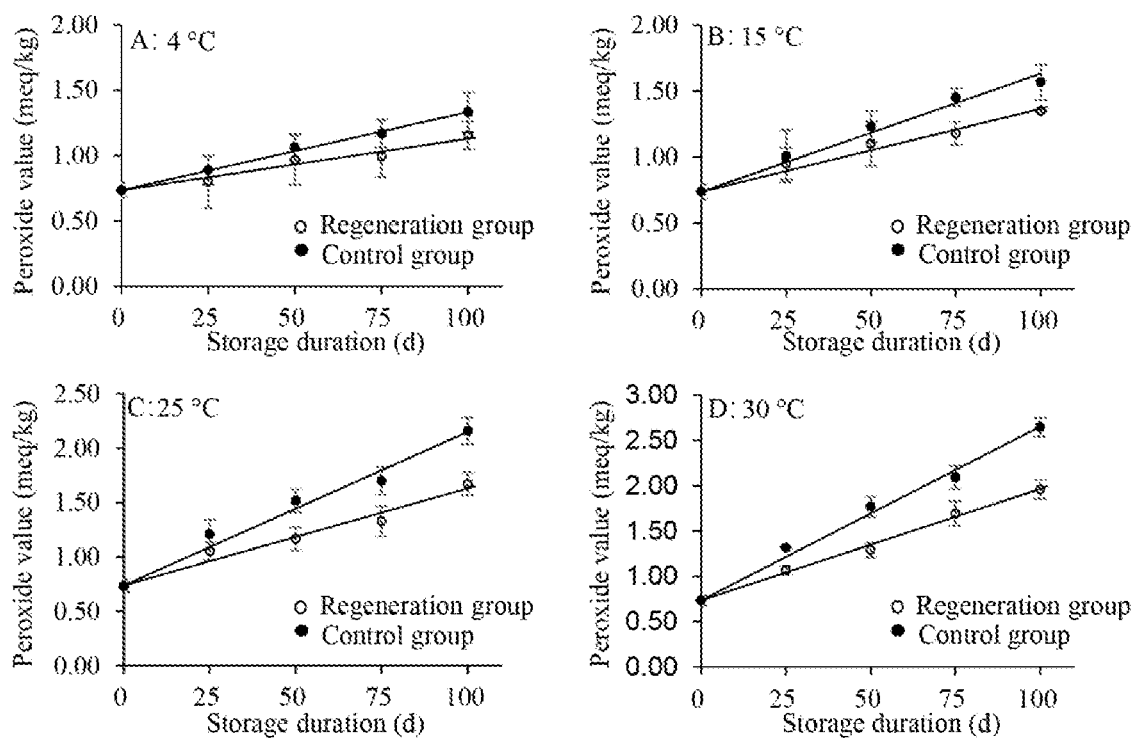
FIG. 2

METHOD FOR VERIFYING REGENERATION EFFECT BETWEEN ANTIOXIDANTS THROUGH ESTABLISHING A SEPARABLE REGENERATION SYSTEM

TECHNICAL FIELD

The invention belongs to the field of regeneration effects of antioxidants and specifically relates to a method for verifying regeneration effect between antioxidants through establishing a separable regeneration system.

BACKGROUND

Antioxidant is a hot topic in both academic research and industrial application. Based on its solubility, antioxidants are normally divided into two groups: water-soluble antioxidant and lipid-soluble antioxidant. Some examples of typical water-soluble antioxidants include: ascorbic acid (AA), tea polyphenol, etc.; and some examples of lipid-soluble antioxidants are tert-butyl hydroquinone (TBHQ), tocopherol, soy lecithin, etc.

In practical applications, using antioxidant alone often fails to meet the requirements of actual production. Therefore, more and more studies are focusing on exploring different combinations of antioxidants with different properties such as solubility, so as to achieve a better antioxidant capacity. It is defined the synergetic effect between two antioxidants when antioxidant capacity of them becomes stronger than that of only one antioxidant. Currently, mechanisms of synergetic effect between two antioxidants including: 1) regenerating between the antioxidants, 2) reducing the formation of peroxide free radical, and 3) chelating metal ions. Among these, the regeneration effect is normally considered as the most important synergetic mechanisms between two antioxidants.

It is indicated that the regeneration effect between two antioxidants with similar solubility is the most reported in recent studies; however, it is occasionally happed when the two antioxidants have significant different solubility. Food systems normally contain both water and lipids. Therefore, it is worthy to explore some novel combinations of food-grade antioxidants with different solubilities, and then extend their applications to the food systems.

Currently, it is limited to establish model systems that can prove the regeneration effect between two antioxidants. Normally, antioxidants are added into carriers with similar solubility simultaneously, e.g. plant oil, fish oil, water, etc. The regeneration effect is subsequently determined through comparing their increase of oxidation parameters. Although the above method can be used to verify the regeneration effect between two antioxidants, its operation is complicated and many interference factors are existed, its accuracy is very limited as well. Thus, it is not conducive to the effective verification of regeneration effect between the antioxidants.

BRIEF SUMMARY OF THE INVENTION

In order to resolving the problems described previously, the present intention developed a method for verifying regeneration effect between antioxidants which is simple in operation, less interference factors, and intuitive and efficient. Another purpose of the present invention is to realize good application of the combination of the two antioxidants in two-phase and multi-phase food systems through verifying regeneration effect between different antioxidants with different solubilities. For achieving the above purposes, the following technical solution is adopted by the invention:

The embodiment of the invention provides a method for verifying regeneration effect between antioxidants through establishing a separable system with antioxidants, comprising the following steps:

(1) Preparation of a separable aqueous phase with water-soluble antioxidant: completely dissolving water-soluble antioxidant into deionized water, and then obtaining a separable aqueous phase with the antioxidant.

(2) Preparation of a separable thermoplastic resin film with lipid-soluble antioxidant.

(2.1) Preparation of thermoplastic resin film: thermoplastic resin masterbatch without antioxidant is first hot-melt extruded into a 1.50-3.00 mm thick thermoplastic resin film using an open type rubber mixer; the 1.50-3.00 mm thick thermoplastic resin film is then placed on a high temperature resistant polyimide film, and is pressed by a flat vulcanizer into a thermoplastic resin film with thickness of 0.10-0.20 mm;

(2.2) Preparation of thermoplastic resin film with lipid-soluble antioxidant: cutting the prepared thermoplastic resin films in step (2.1) into two pieces; placing lipid-soluble antioxidant between them, and combining the antioxidant with the two thermoplastic resin films; cutting the same thermoplastic resin films into many small pieces and hot-pressing them; repeating the cutting and hot-pressing procedures for 3-5 times.

(2.3) Storage and reserve: washing the thermoplastic resin films with lipid-soluble antioxidant in step (2.2) by water; drying the thermoplastic resin films with lipid-soluble antioxidant in an oven at 25° C. for 24 h; sealing and storing it in a refrigerator at 4° C. before use.

(3) Verification of regeneration effect between two antioxidants in the separable regeneration system.

(3.1) Setup of regeneration group: cutting one piece of the thermoplastic resin film with lipid-soluble antioxidant prepared in step (2), and transferring it into the aqueous phase with water-soluble antioxidant prepared in step (1) as regeneration group. The surface area of thermoplastic resin film with lipid-soluble antioxidant is recorded as S, the weight of thermoplastic resin film with lipid-antioxidant is recorded as in;

(3.2) Setup of control group: cutting one piece of the thermoplastic resin film without adding lipid-soluble antioxidant with surface area S and weight in; transferring it into the aqueous phase prepared in step (1) as control group.

(3.3) Verification of regeneration effect: sealing the two reactors of regeneration group and control group; determining antioxidant capacity of aqueous phase in both groups after same reaction duration through scavenging hydroxyl radical method. When the antioxidant capacity of regeneration group is significantly higher than that of control group, it is proved that the added lipid-soluble antioxidant is capable of regenerating the antioxidant in aqueous phase; otherwise, it is proved that the antioxidant in aqueous phase is capable of regenerating the lipid-soluble antioxidant in the thermoplastic resin film. The regeneration effect does not exist between two antioxidants when no difference is observed between two groups.

In step (2.1), certain specific embodiments, the parameters of the open type rubber mixer are as follows: operation temperature of the front drum is 150-175° C., and that of the rear drum is 150-175° C.; and drum space is 1.50-3.00 mm.

In certain specific embodiments, the step (2.1), the parameters of flat vulcanizer are as follows: operation temperature of the upper and lower plats is 145-160° C.; and operation pressure is 1000-1400 Pa.

In step (3.3), certain specific embodiments, the reaction temperature after sealing the reactor in the step (3.3) is ranging from 10-30° C.

In step (3.3), certain specific embodiments, the scavenging hydroxyl radical method in the step (3.3) further comprises the sub-steps as follows: taking 1 mL of antioxidant aqueous-solution, adding 0.5 mL of salicylic acid solution at 12 mmol/L, 0.5 mL of $FeSO_4$ aqueous solution at 0.9 mol/L, 0.5 mL of $H_2O_2$ aqueous solution at 9 mmol/L; reacting at 37° C. for 1 h in water bath and there are sediments exist in the lower layer; taking 1 mL of upper solution and diluting it to 4 mL with deionized water; measuring absorbance value at 510 nm.

In certain specific embodiments, the thermoplastic resin film is made by either polyethylene (PE) or polyvinyl chloride (PVC).

In certain specific embodiments, the method of combining lipid-soluble antioxidant into the thermoplastic resin films include hot pressing, mixing, and extruding process.

In certain specific embodiments, the method of verifying regeneration effect between two antioxidants in the separable regeneration system can only measure one parameter, i.e. antioxidant capacity of aqueous phase, for indicating whether the regeneration effect is happened. Because the lipid-soluble antioxidant on the thermoplastic resin film is insoluble in the aqueous phase, but contact with water, therefore, the change of water-soluble antioxidant content in aqueous phase can be characterized by measuring the change of antioxidant capacity in aqueous phase, which makes it easier and more intuitive to verify whether there is regeneration between the two soluble antioxidants. Compared with the prior art, the present invention has following advantages:

1. The separable regeneration system established in present invention can avoid interference on determining antioxidant capacity of each antioxidant after mixing them. The operation is also simple and easy to be conducted.
2. The scavenging hydroxyl radical method adopted in present invention for determining antioxidant capacity of aqueous phase can measure the change of antioxidant capacity in aqueous phase, namely, can characterize water-soluble antioxidant content in the aqueous phase. The operation is simple, and has a low cost.
3. Many controllable variables exist in the separable system, and the variables of separable system can be adjusted according to actual requirements to prove whether there is regeneration effect between two antioxidants under specific reaction conditions.
4. The antioxidant combinations with regeneration effect verified through the separable system can be applied to two-phase or multi-phase food systems, e.g. water-in-oil system, oil-in-water system, etc.
5. Antioxidant combinations with regeneration effect verified through the separable system can be further applied to the food system as follows: one of the antioxidants is first added into the food, and the other is added into the food package. The shelf life of the well-packed food will be extended due to the regeneration effect between two antioxidants.

BRIEF DESCRIPTION OF THE DRAWINGS

FIG. 1 is a schematic of establishing the regeneration system.

FIG. 2 respectively shows peroxide value in liquor chocolate of regeneration group and control group at four temperature levels: A: 4° C.; B: 15° C.; C: 25° C.; D: 30° C.

DETAILED DESCRIPTION OF THE INVENTION

A further detailed description of the technical solution of the invention is given as follows with embodiments and accompanying drawings, however, the invention is not only limited to the following embodiments.

Embodiment 1 Verifying Regeneration Effect Between AA and TBHQ

In certain specific embodiments, the method for verifying regeneration effect between AA and TBHQ through the separable system comprises the following steps:
(1) Preparing a Separable PE Film with TBHQ PE masterbatch without antioxidant was hot-melt extruded into a PE film with thickness of 2 mm using open type rubber mixer (setting parameters of rubber mixer were as follows: operation temperature of the front drum was 155° C. and that of the rear drum was 155° C.; drum space was 2.00 mm); 2.0 g of PE film with thickness of 2.00 mm was placed on the surface of high temperature resistant polyimide film and was hot-pressed into 0.15 mm using flat vulcanizer (setting parameters of flat vulcanizer were as follows: operation temperature of the upper and lower plats was 155° C., and operation pressure was 1200 Pa); in order to make the TBHQ distribution in the PE film uniform, the pre-weighed TBHQ must be incorporated into the PE film by a vulcanizer, and after that the same film needs to be cut and hot pressed four times for getting the PE film with TBHQ; the PE film with TBHQ manufactured by the above method was washed for multiple times with deionized water; the PE film with TBHQ was dried in an oven at 25° C. for 24 h; the PE film with TBHQ was sealed and stored at 4° C. before use.

(2) Establishing a Separable Regeneration System 100 mg AA was completely dissolved in 100 mL deionized water, and an aqueous solution of AA at concentration of 1.0 g/L was obtained; 30 mL of AA aqueous solution was transferred into a 100 mL stopper flask; PE film with TBHQ prepared in the step (1) was added into the stopper flask in certain surface area and weight, which was used as regeneration group; PE film without TBHQ that has the same surface area and weight was added into another stopper flask with 30 mL of AA aqueous solution as control group; after the stopper flasks of both regeneration group and control group were sealed, the reaction was carried out at 25° C.

(3) Verifying Regeneration Effect Between AA and TBHQ 1 mL of AA aqueous solution from both regeneration group and control group were collected at different time; 1 mL of AA aqueous solution was mixed with 0.5 mL of salicylic acid solution at 12 mmol/L, 0.5 mL of $FeSO_4$ aqueous solution at 0.9 mol/L, 0.5 mL of $H_2O_2$ aqueous solution at 9 mmol/L; after 1 h of water bath at 37° C., 1 mL of solution from upper layer was collected (there exist sediments in the lower layer) and was diluted to 4 mL, and the absorbance value was measured at 510 nm. Regeneration effect between AA and TBHQ can be verified through comparing the difference of antioxidant capacity between AA aqueous solution collected from regeneration group and control group. The separable system for verifying regeneration effect between AA and TBHQ is shown in FIG. 1.

Embodiment 2 Combination of TBHQ and AA is Further Applied to the Liquor Chocolate According to the Verified Regeneration Effect Between AA and TBHQ in the Separable System In certain specific embodiments, according to the verified regeneration effect between AA and TBHQ in the separable system, combination of TBHQ and AA is further applied to the liquor chocolate that comprises the following steps:

(1) Preparing liquor chocolate shell: 40% black chocolate was crushed and completely melted in a food-grade vessel at 70° C. in water bath; pre-weighted food-grade TBHQ powder was added into the vessel, the mixture was blended and 0.20 g TBHQ/kg chocolate syrup was obtained and stored at room temperature before use, which was used as the shell material of regeneration group. Meanwhile, a liquor chocolate shell without adding TBHQ was prepared as control group.

(2) Preparing chocolate liquid filling: milk chocolate, 45% food-grade ethanol aqueous solution, light cream, and butter were added in a weight ratio of 30:20:20:3, and then mixed well at 40° C.; AA was added into the liquid filling at concentration of 1 g/L (based on the moisture content of the liquid filling); and then cooled down to the room temperature. Both the regeneration group and the control group have the same filling.

(3) Preparing liquor chocolate: the chocolate shell material was poured into a mold; the excess chocolate was poured out when the out layer of chocolate is solidified; the filling was poured into the mold which was then sealed with the shell material; the mold was stored in a refrigerator for 30 min at 4° C. and the mold was removed.

(4) Conducting Accelerated Storage Experiment of Liquor Chocolate

The liquor chocolates of regeneration group and control group were respectively stored at temperature of 4° C., 15° C., 25° C. and 30° C. for accelerated storage experiment.

(5) Extracting Lipids from Liquor Chocolate:

The liquor chocolate was placed into a stopper flask and melted at 60° C., and then cooled down for 5 min at the room temperature before petroleum ether into was poured into the flask and lipids extracted at 25° C. for 12 h; the filtrate was collected by conducting filtration using a fast-qualitative filter paper containing anhydrous sodium sulfate; the filtrate was conducted rotary evaporation at 35° C. for 15 min, and lipids in the liquor chocolate was obtained after blowing nitrogen for 10 min (6) Measuring Peroxide Value of Liquor Chocolate Measuring peroxide value of liquor chocolate according to the titration method of national standard GB 5009.227-2016 Food Safety National Standard for the Determination of Peroxide Value in Foods:

The extracted lipids from liquor chocolate with the weight of 2-3 g (accurate to 0.001 g) is transferred into an iodine flask with the volume of 250 mL; 30 mL of mixed liquor of trichloromethane and ice acetic acid liquor (with the volume ratio of 40:60) is added, and the iodine flask is oscillated slightly to make lipids be completely dissolved. One mL of the saturated potassium iodide solution is added accurately, the flask cap is tightly screwed, and the iodine flask is oscillated slightly for 0.5 min and placed in a dark place for 3 min. The iodine flask is taken out from the dark place, then 100 mL of water is added into the iodine flask. After uniform oscillation, separated-out iodine is titrated instantly with a sodium thiosulfate standard solution (the standard solution with the concentration of 0.002 mol/L is used when the estimated peroxide value is 0.15 g/100 g or less; and the standard solution with the concentration of 0.01 mol/L is used when the estimated peroxide value is higher than 0.15 g/100 g). One mL of 1% starch indicator is added when the iodine is titrated to be faint yellow, and titration continues to be conducted with violent oscillation until the blue color of the solution disappeared. Meanwhile, a blank test as control is conducted. The volume $V_0$ of the sodium thiosulfate solution consumed by the blank test cannot be higher than 0.1 mL.

$$X_1(\text{mmol/kg}) = C \times (V - V_0) \times 0.1269 \times 100/m$$

$X_1$— the peroxide value, unit: g/100 g
V—the volume of the sodium thiosulfate standard solution consumed by the sample, unit: mL
$V_0$— the volume of the sodium thiosulfate standard solution consumed by the blank test, unit: mL
C—the concentration of the sodium thiosulfate standard solution, unit: mol/L
0.1269—the mass of iodine corresponding to 1.00 mL of the sodium thiosulfate standard titration solution [$C(Na_2S_2O_3)$ =1.000 mol/L]
m—mass of the sample, unit: g
100—the conversion coefficient Results: The combination of TBHQ-AA in the liquor chocolate can effectively slow down the increase in peroxide value. The results are shown in FIG. 1.

FIG. 2: Peroxide values of the liquor chocolate in the regeneration group and the control group (A: 4° C.; B: 15° C.; C: 25° C.; D: 30° C.)

In summary, the separable regeneration system established by the present invention can effectively verify the regeneration effect between different antioxidants, and has the advantages of simple operation, less interference factors, intuitive and high efficiency. The experimental results show that the antioxidant combination with regeneration effect has good antioxidant effect in food system.

The invention claimed is:
1. A method for verifying regeneration effect between antioxidants through establishing a separable regeneration system comprising the steps:
(1) preparing an aqueous phase of separable regeneration system: completely dissolving water-soluble antioxidant into deionized water, and then obtaining aqueous solution of water-soluble antioxidant, that is aqueous phase of separable regeneration system;
(2) preparing a separable thermoplastic resin film with lipid-soluble antioxidant
(2.1) preparing thermoplastic resin film: thermoplastic resin masterbatch without antioxidant is first hot-melt extruded into a thermoplastic resin film with thickness of 1.5-3.0 mm using an open type rubber mixer; the 1.5-3.0 mm thermoplastic resin film is placed on a resistant polyimide film, and is pressed by a flat vulcanizer into one thermoplastic resin film with thickness of 0.10-0.20 mm;
(2.2) preparing thermoplastic resin film with lipid-soluble antioxidant: cutting a prepared 0.10-0.20 mm thermoplastic resin film in step (2.1) into two pieces; placing lipid-soluble antioxidant between the two pieces of thermoplastic resin films, and combining the lipid-soluble antioxidant with the two pieces of thermoplastic resin films, thus obtaining a whole piece of thermoplastic resin film; cutting the whole piece of thermoplastic resin film into two pieces and hot-pressing them into a whole piece of film; repeating the cutting and hot-pressing procedure for 3-5 times;

(2.3) storage and reserve: washing the prepared thermoplastic resin film with lipid-soluble antioxidant prepared in step (2.2) with water; drying the thermoplastic resin film with lipid-soluble antioxidant in an oven at 25° C. for 24 h; sealing and storing the films in a refrigerator at 4° C. before use;

(3) verification of regeneration effect between antioxidants in the separable regeneration system (3.1) setup of regeneration group: transferring the thermoplastic resin film with lipid-soluble antioxidant prepared in step (2.3) into the aqueous phase of separable regeneration system prepared in step (1) as regeneration group, a surface area of the thermoplastic resin film with lipid-soluble antioxidant is recorded as S, a weight of the thermoplastic resin film with lipid-soluble antioxidant is recorded as m;

(3.2) setup of control group: transferring the thermoplastic resin film without lipid-soluble antioxidant from step (2.1) with surface area S and weight m into the aqueous phase of separable regeneration system prepared in step (1) as control group;

(3.3) verification of regeneration effect: sealing reactors of regeneration group and control group; measuring antioxidant capacity of aqueous phase in both groups after same reaction duration through scavenging hydroxyl radical method; when antioxidant capacity of regeneration group is significantly higher than that of control group, it is proved that the added lipid-soluble antioxidant is capable of regenerating the antioxidant in aqueous phase; otherwise, it is proved that the antioxidant in aqueous phase is capable of regenerating the lipid-soluble antioxidant in the thermoplastic resin film; wherein the regeneration effect does not exist between the antioxidant in the aqueous phase and the lipid-soluble antioxidant when no difference in antioxidant capacity is observed between the regeneration group and the control group.

2. The method according to claim 1, wherein in the preparing thermoplastic resin film in the step (2.1), parameters of open type rubber mixer is set as follows: operation temperature of a front drum is 150-175° C. and that of a rear drum is 150-175° C.; drum space is 1.5-3.0 mm; parameters of flat vulcanizer is set as follows: operation temperature of upper and lower plats is 145-160° C.; and operation pressure is 1000-1400 Pa.

3. The method according to claim 1, wherein reaction temperature after sealing the reactors in step (3.3) is ranging from 10-30° C.

4. The method according to claim 3, wherein the scavenging hydroxyl radical method in the step (3.3) further comprises the sub-steps as follows: adding 1 mL of antioxidant aqueous-solution into 0.5 mL of salicylic acid solution at 12 mmol/L, 0.5 mL of $FeSO_4$ aqueous solution at 0.9 mol/L, 0.5 mL of $H_2O_2$ aqueous solution at 9 mmol/L and reacting at 37° C. for 1 h in water bath and there exist sediments in a lower layer; taking 1 mL of upper solution and diluting it to 4 mL; measuring an absorbance value of the diluted upper solution at 510 nm.

5. The method according to claim 3, wherein the thermoplastic resin film is made by either polyethylene or polyvinyl chloride.

6. The method according to claim 1, wherein the scavenging hydroxyl radical method in the step (3.3) further comprises the sub-steps as follows: adding 1 mL of antioxidant aqueous-solution into 0.5 mL of salicylic acid solution at 12 mmol/L, 0.5 mL of $FeSO_4$ aqueous solution at 0.9 mol/L, 0.5 mL of $H_2O_2$ aqueous solution at 9 mmol/L and reacting at 37° C. for 1 h in water bath and there exist sediments in a lower layer; taking 1 mL of upper solution and diluting it to 4 mL; measuring an absorbance value of the diluted upper solution at 510 nm.

7. The method according to claim 6, wherein the thermoplastic resin film is made by either polyethylene or polyvinyl chloride.

8. The method according to claim 1 wherein the thermoplastic resin film is made by either polyethylene or polyvinyl chloride.

9. The method according to claim 8, wherein the method of combining the lipid-soluble antioxidant with the two pieces of the thermoplastic resin films in step (2.2) includes hot pressing, mixing, and extruding processes.

10. The method according to claim 1, wherein the method of combining the lipid-soluble antioxidant with the two pieces of the thermoplastic resin films in step (2.2) includes hot pressing, mixing, and extruding processes.

* * * * *